US00PP25748P3

(12) United States Plant Patent
Dobres

(10) Patent No.: US PP25,748 P3
(45) Date of Patent: Jul. 28, 2015

(54) ***VERONICA* PLANT NAMED 'NOVAVERPIN'**

(50) Latin Name: *Veronica spicata*
Varietal Denomination: Cv. Novaverpin

(71) Applicant: CP DELAWARE, INC., Wilmington, DE (US)

(72) Inventor: Michael S. Dobres, Philadelphia, PA (US)

(73) Assignee: CP Delaware, Inc., Wilmington, DE (US)

( * ) Notice: Subject to any disclaimer, the term of this patent is extended or adjusted under 35 U.S.C. 154(b) by 97 days.

(21) Appl. No.: 13/998,768

(22) Filed: Dec. 4, 2013

(65) Prior Publication Data

US 2015/0156940 P1 Jun. 4, 2015

(51) Int. Cl.
*A01H 5/00* (2006.01)

(52) U.S. Cl.
USPC ..... Plt./251

(58) Field of Classification Search
USPC ..... Plt./251
See application file for complete search history.

*Primary Examiner* — Susan McCormick Ewoldt
(74) *Attorney, Agent, or Firm* — Buchanan, Ingersoll & Rooney PC

(57) ABSTRACT

The new plant resulted as a mutation of the 'Tickled Pink' cultivar (U.S. Plant Pat. No. 16,182) that was induced by exposure to gamma irradiation followed by selection. Attractive light pink blossoms are formed in abundance with a propensity to rebloom following trimming in the absence of a vernalization requirement for flowering. A dense compact mounding growth habit is displayed. The stems that bear flowers are substantially upright. The plant is well suited for providing attractive ornamentation in the landscape.

2 Drawing Sheets

Botanical/commercial classification: *Veronica spicata/ Veronica* Plant.

Varietal denomination: cv. Novaverpin.

SUMMARY OF THE INVENTION

The new plant of the present invention was derived from the 'Tickled Pink' cultivar (U.S. Plant Pat. No. 16,182) at West Grove, Pa., U.S.A. During September 2008, open-pollinated seeds were collected from 'Tickled Pink' plants. The seeds were thereafter subjected to gamma irradiation in order to seek to induce various mutations. Following the gamma irradiation, the irradiated seeds were sown under greenhouse conditions during January 2009, and the resulting plants were found during the following spring and summer to differ from each other in many ways. A single plant of the present invention was selected and was preserved in view of its unique combination of attractive phenotypic characteristics. Had this plant not been created, identified and preserved it would have been lost to mankind.

It was found that the new *Veronica* plant of the present invention displays the following combination of characteristics:

(a) exhibits a dense compact mounding growth habit,
(b) forms upright stems,
(c) is lacking a vernalization requirement for flowering,
(d) forms in abundance attractive light pink blossoms with a propensity to rebloom following trimming, and
(e) is well suited for providing attractive ornamentation in the landscape.

During observations to date, the plant has been found to be hardy in U.S.D.A. Hardiness Zone No. 6. No further definitive hardiness information has been obtained.

The new cultivar well meets the needs of the horticultural industry and can be grown to advantage as a perennial garden plant to provide colorful ornamentation. For instance, it can be grown in parks, gardens and residential settings.

Plants of the new cultivar can be readily distinguished from other *Veronica spicata* cultivars including its parent. More specifically, the 'Tickled Pink' cultivar forms bright pink blossoms instead of blossoms having the light pink coloration of the new cultivar.

The new cultivar also can be readily distinguished from the 'Rotfuchs' cultivar (non-patented). Unlike the new cultivar, the 'Rotfuchs' cultivar forms dark pink blossoms and has been found to require vernalization during observations at West Grove, Pa., U.S.A.

The rooting of cuttings has been used to asexually propagate the new cultivar at West Grove, Pa., U.S.A. It has been found that the characteristics of the new cultivar are stable and are reliably transmitted from one generation to another. Accordingly, the new cultivar can be asexually reproduced in a true-to-type manner.

The new cultivar of the present invention has been named 'Novaverpin', and will be maketed under the PINK MOODY BLUES Trademark.

BRIEF DESCRIPTION OF THE PHOTOGRAPHS

The accompanying photographs illustrate the new cultivar in color as nearly true as it is reasonably possible make the same in color illustrations of this nature. The plants were approximately two years of age and were being grown on their own roots at West Grove, Pa., U.S.A.

DETAILED BOTANICAL DESCRIPTION

Figure 1:
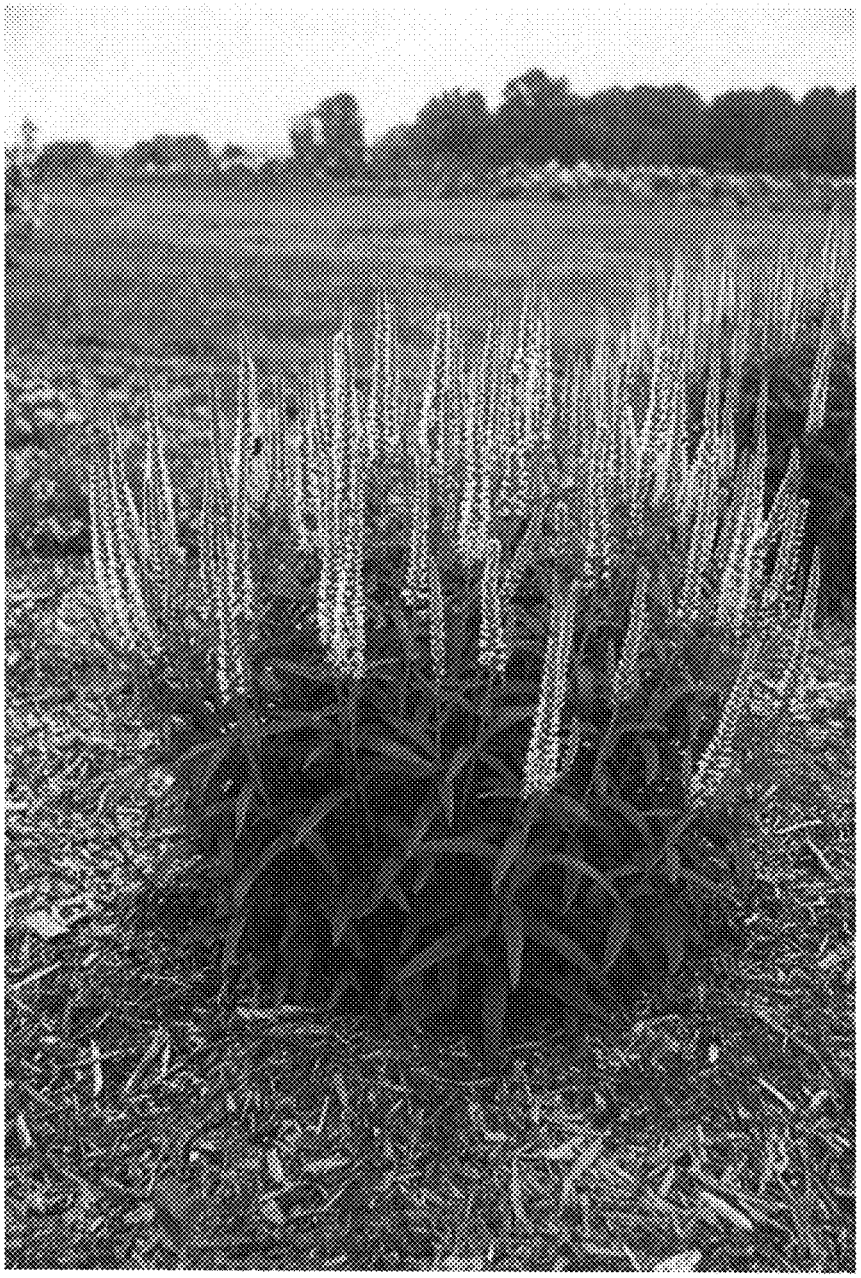
FIG. 1 illustrates a specimen of a typical mature flowering plant of the new cultivar while growing outdoors in full sun. The typical upright dense compact mounding growth habit is shown.
Figure 2:
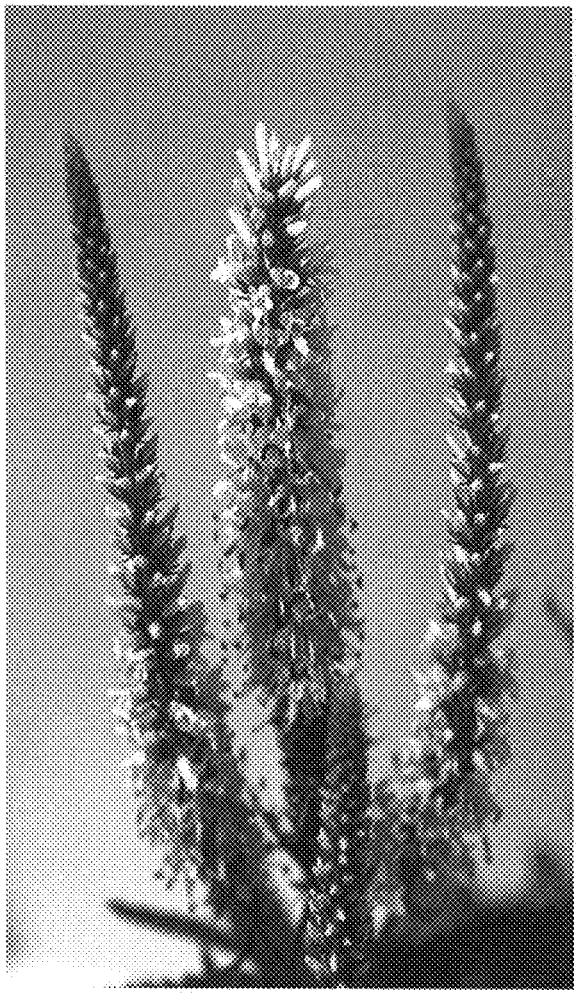
FIG. 2 illustrates a closer view of the flowers on upright stems of the new cultivar in various stages of development. The plant was being grown in a container.

The following is a detailed description while observing two-year-old plants of the new cultivar that were produced by the rooting of cuttings. Such plants were grown in containers under greenhouse conditions at West Grove, Pa., U.S.A. The chart used in the identification of color is the R.H.S. Colour Chart (1995 Edition or equivalent) of The Royal Horticultural Society, London, England. Common color terms are to be accorded their customary dictionary significance.

Botanical classification: *Veronica spicata*, cv. Novaverpin.

*Parent.*—*Veronica spicata*, cv. 'Tickled Pink'.

*Plant type*.—Herbaceous perennial.

Plant:

*Growth habit*.—Dense compact and mounding.

*Height*.—Approximately 41 cm on average when grown in a container, and approximately 66 cm on average when grown in the ground.

*Spread*.—Approximately 38 cm on average when grown in a container, and approximately 63.5 cm on average when grown in the ground.

*Branching*.—Commonly approximately 3 to 7 lateral stems arise from a mat of congested basal stems.

*Branching angle*.—Commonly approximately 40 degrees.

*Stem length*.—Commonly approximately 30 cm on average.

*Stem diameter*.—Commonly approximately 2 mm on average.

*Stem shape*.—Substantially round in cross-section.

*Stem color*.—Near Green Group 139C.

*Stem texture*.—Finely pubescent surface.

*Internode length*.—Commonly approximately 2.5 cm.

*Roots*.—Fibrous network.

Foliage:

*Arrangement*.—Opposite.

*Shape*.—Obovate to elliptic.

*Apex*.—Obtuse.

*Base*.—Acuminate.

*Length*.—Commonly approximately 8.5 cm on average for lower leaves, and approximately 5 cm on average for upper leaves.

*Width*.—Commonly approximately 2 cm on average for lower leaves and approximately 1.3 cm on average for upper leaves.

*Texture*.—On the upper surface sparsely pubescent, and on the under surface sparsely pubescent with moderate pubescence on the veins.

*Color*.—On the upper surface near Green Group 139A, and on the lower surface near Green Group 137A.

*Margins*.—Entire and somewhat crenate.

*Venation*.—Pinnate and near Yellow-Green Group 144A in coloration.

*Fragrance*.—None noticeable.

*Petiole*.—Commonly approximately 2 cm in length on average, approximately 2 mm in diameter on average, finely pubescent, and near Yellow-Group 144C in coloration.

*Stipules*.—Absent.

Inflorescence:

*Time*.—Commonly May through July with good rebloom following trimming.

*Type*.—Single arranged in upright racemes.

*Buds*.—Elongated ovoid, approximately 5 mm in length just before opening, approximately 1.5 mm in diameter, and near Red-Purple Group 62D in coloration.

*Quantity*.—Free-flowering, commonly 1 to 5 flowering racemes per lateral branch, and commonly approximately 120 open flowers per inflorescence.

*Racemes*.—Approximately 12 cm in length on average, and approximately 2 cm in width on average.

*Flower diameter*.—Approximately 8 mm.

*Flower length*.—Approximately 7 mm.

*Aspect*.—Commonly approximately 30 degrees prior to opening and substantially horizontal when fully open.

*Corolla configuration*.—Funnel-formed with petals fused into a tube towards the base.

*Petal number*.—Four.

*Petal tube*.—Approximately 2 mm in length on average, approximately 2 mm in width on average, glabrous in texture, and near Red-Purple Group 69D in coloration.

*Petal lobes*.—Approximately 5 mm in length on average, approximately 3 mm in width on average, glabrous in texture, broadly linear in configuration, entire margins, rounded apex, and near Red-Purple Group 69B on the upper and under surfaces.

*Sepal arrangement*.—Four in number, fused at base.

*Sepal shape*.—Triangular-ovate.

*Sepal length*.—Approximately 2 mm on average.

*Sepal diameter*.—Approximately 1 mm on average.

*Sepal apex*.—Acute.

*Sepal margin*—Entire.

*Sepal texture*.—Smooth.

*Sepal color*.—Near Green Group 137B on the upper surface and near Green Group 137C on the under surface.

*Stamen number*.—Two.

*Anther shape*.—Ovoid.

*Anther length*.—Approximately 2 mm on average.

*Anther width*.—Approximately 1 mm on average.

*Anther color*.—Near Red-Purple Group 75A.

*Filaments*.—Commonly approximately 6 mm in length on average, commonly less than 1 mm in diameter on average, and near White Group 155B in coloration.

*Pollen*.—Present in a moderate quantity and near Greyed-Yellow Group 162D in coloration.

*Pistil number*.—One, with stigma and style not being readily distinguishable.

*Shape*.—Filiform.

*Color*.—Near Red-Purlpe. Group 70B.

*Length*.—Approximately 6 mm.

*Width*.—Commonly less than 1 mm.

*Ovary shape*.—Rounded.

*Ovary length*.—Approximately 1.5 mm on average.

*Ovary width*.—Approximately 1 mm on average.

*Ovary color*.—Near Green Group 142B.

*Seed number*.—Commonly 4 or less.

*Seed shape*.—Ovoid and commonly with flattening.

*Seed length*.—Approximately 1 mm on average.

*Seed diameter*.—Approximately 0.5 mm on average.

*Seed width*.—Less than 1 mm.

*Seed color*.—Greyed-Brown Group 199B.

*Fragrance*.—None observed.

*Flower longevity*.—Approximately 8 days on the plant.
*Peduncle length*.—Approximately 1 cm on average.
*Peduncle diameter*.—Substantially round and approximately 1 mm on average.
*Peduncle texture*.—Finely pubsecent.
*Peduncle color*.—Near Green Group 139C.
*Pedicel length*.—Very short, and commonly approximately 0.05 mm.
*Pedicel width*.—Commonly less than 1 mm.
*Pedicel texture*.—Smooth.
*Pedicel color*.—Near Green Group 143B.

Disease resistance: No particular resistance to pathogens and pests common to *Veronica* plants has been encountered during observations to date.

Plants of the 'Novaverpin' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct *Veronica* plant having the following combination of characteristics:

(a) exhibits a dense compact mounding growth habit,
(b) forms upright stems,
(c) is lacking a vernalization requirement for flowering,
(d) forms in abundance attractive light pink blossoms with a propensity to well rebloom following trimming, and
(e) is well suited for providing attractive ornamentation in the landscape;

substantially as illustrated and described.

* * * * *